United States Patent
Schiller

[19]

[11] Patent Number: 6,010,472
[45] Date of Patent: Jan. 4, 2000

[54] FRAME-CONSTRUCTION HYPER-EXTENSION ORTHESIS

[75] Inventor: Roland Schiller, Schnaittach, Germany

[73] Assignee: Weihermuller & Voigtmann GmbH & Co., Bayreuth, Germany

[21] Appl. No.: 08/930,997

[22] PCT Filed: Apr. 20, 1996

[86] PCT No.: PCT/DE96/00695

§ 371 Date: Mar. 16, 1998

§ 102(e) Date: Mar. 16, 1998

[87] PCT Pub. No.: WO96/32910

PCT Pub. Date: Oct. 24, 1996

[30] Foreign Application Priority Data

Apr. 21, 1995 [DE] Germany ............ 295 06 989 U

[51] Int. Cl.[7] ........................................ A61F 5/02
[52] U.S. Cl. ............................... 602/19; 128/102.1
[58] Field of Search ............................. 602/16, 19, 18; 128/95.1, 96.1, 97.1, 98.1, 99.1, 100.1, 102.1, 103.1, 104.1, 105.1, 106.1, 107.1

[56] References Cited

U.S. PATENT DOCUMENTS

| | | | |
|---|---|---|---|
| 1,793,776 | 2/1931 | Clayton | 602/19 |
| 1,917,106 | 7/1933 | Ettinger | 602/19 |
| 2,310,566 | 2/1943 | Anderson | 602/19 |
| 2,871,850 | 2/1959 | Peckham | 602/19 |

*Primary Examiner*—Richard J. Apley
*Assistant Examiner*—Kim M. Lee
*Attorney, Agent, or Firm*—Eric P. Schellin

[57] ABSTRACT

A frame-construction hyperextension orthotic device with several truss pads resting on the patient's body is described in which the individual rod elements (13, 14) provided with oblong holes (14) can be adapted in a continuously adjustable manner to the individual requirements and can be stopped in the desired position by setscrews (17).

2 Claims, 2 Drawing Sheets

FRAME-CONSTRUCTION HYPER-EXTENSION ORTHESIS

BACKGROUND OF THE INVENTION

The invention is relative to a frame-construction hyperextension orthotic device.

Orthotic devices of this type serve among other things in the case of traumatic compression fractures in the lumbar and thoracolumbar area as well as in the thoracic area, adolescent kyphosis and osteoporosis as well as postoperatively to stabilize the patient and to prevent certain damaging movements of the patients such as excluding inclining or rotating movements of the spinal column and to make it possible to relieve stress from the frontal edges of the spinal column.

At the same time lateral sideways movements should also be limited.

DESCRIPTION OF THE RELATED ART

The known orthotic devices of this type comprise a 3-point system with a truss pad on the sternum, on the pubic bone as well as one on the thoracolumbar transition. The adaptation to the individual size relationships takes place via rod elements which can be shifted relative to each other and are permanently connected to each other via removable screws.

Frequently, the screws are thrown out almost explosively when they are loosened. On account of this known design with its problems, three to five different sizes are necessary.

BRIEF SUMMARY OF THE INVENTION

The invention has the problem of creating an orthotic device of the initially cited type which assures a reliable elimination of undesired and damaging movements of the patient and nevertheless makes possible, starting from only one orthotic size, if possible, an easy, continuously adjustable adaptation to the particular individual size relationships and/or angular associations of the patient.

The inventions solves this problem by the features of claim 1.

Advantageous developments result from the subclaims.

The invention is explained by way of example in the following with reference made to the drawings.

DETAILED DESCRIPTION OF THE INVENTION

Figure 1:
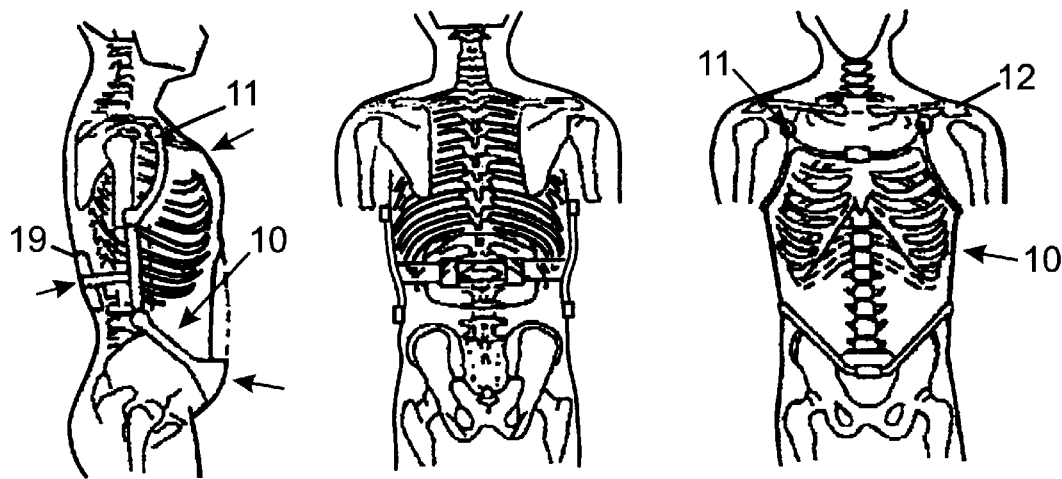
FIG. 1 shows a simplified basic representation of a frame orthotic device with two pressure truss pads just below the particular clavicles.

As can be recognized from FIG. 1, in the case of hyperextension orthotic device 10 in accordance with the invention and in deviation from the previously customary arrangement, pressure points are provided with truss pads 11, 12 not on the sternum but rather higher up just below the two clavicles. This prevents, in a more effective manner than previously, the patient from executing inclining or rotating movements of the vertebra segments. At the same time lateral sideways motions are limited by the frame orthotic device. In addition, lesions up to the level of the eighth thoracic vertebra can be taken care of.

In practice, an easy and continuously adjustable adjustment of rod elements 13, 14 in their longitudinal direction and therewith an easy adaptation to the individual size relationships of the patient are especially significant.

Figure 2:
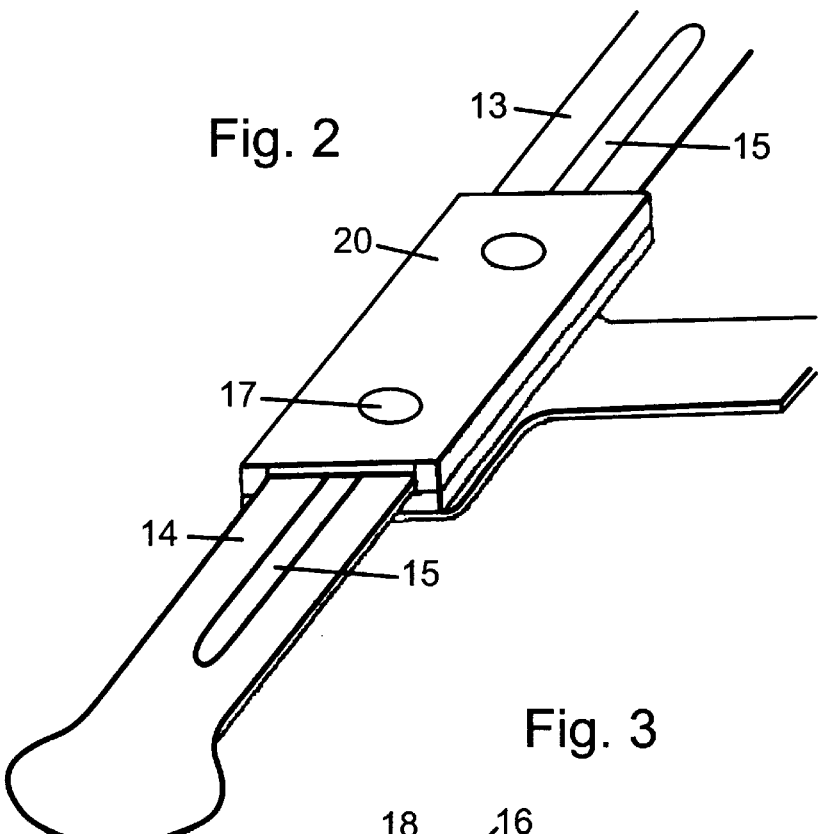
FIG. 2 shows a basic representation of two rod elements with guide body which elements can be shifted longitudinally via oblong holes.
Figure 3:
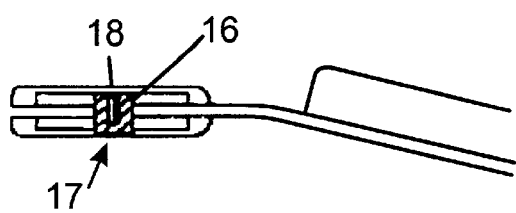
FIG. 3 shows a cross section along line III—III in FIG. 2.
Figure 4:
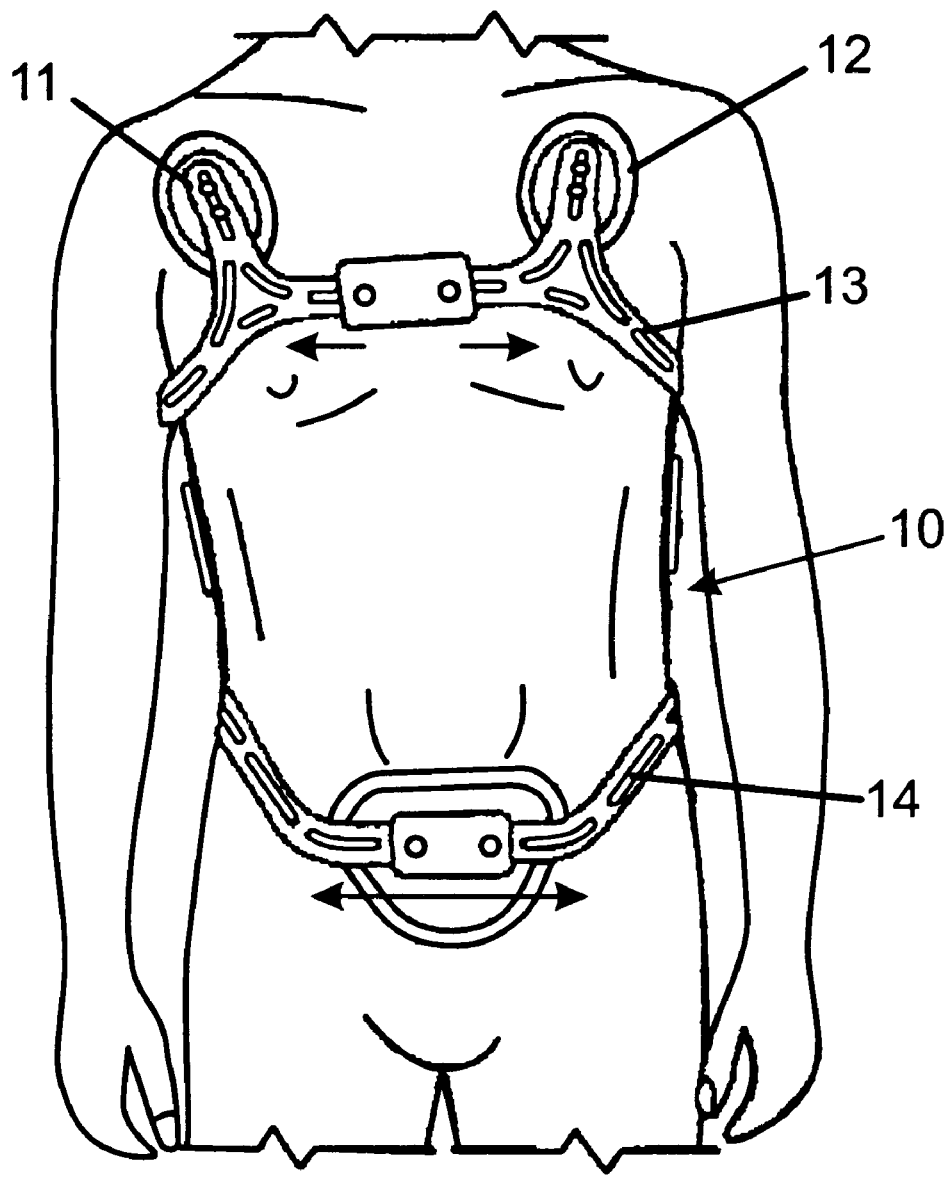
FIG. 4 shows a perspective representation of a variant of the hyperextension orthotic device.

As results from FIG. 2, upper 13 and lower rod elements 14 comprise oblong holes 15 through which outer guide cylinders 16 of setscrews 17 extend with a slight snug fit in accordance with FIG. 3. Guide cylinders 16 of setscrews 17 are provided on the inside with a thread which surrounds threaded pin 18 extending from the other side into guide cylinder 16. This threaded pin 18 has a multiple of the length required to loosen setscrew 17. Setscrew 17 can therefore be considered as "unlosable" since only a fraction of a revolution of setscrew 17 is required to loosen the stop but the overlap of the threads of setscrew 17 and of threaded pin 18 amounts to several threads.

Basically, suitable stops or other suitable motion limitations can also be used to prevent setscrew 17 from loosening from threaded pin 18 in an undesired manner.

Of course, the functions of threaded pin 18 and of setscrew 17 can be exchanged with one another, that is, the stop can take place via an adjustment of threaded pin 18.

The measures described above prevent setscrews 17 and threaded pins 18 from being cast out explosively under the influence of the tensions acting on them when they are loosened.

Other safety mechanisms can also be provided for setscrews 17, e.g., adjustment limitations.

The adjustment mechanisms described above are multiply present on the frame orthotic device. They can be selected in order to adapt the frame orthotic device in length, height and width to the particular individual requirements.

Back truss pad 19 can also be connected via a relatively stiff band or an appropriate belt to the front part of the frame orthotic device.

It is extremely important that the essential purpose, namely, the excluding of the inclining or rotating movement ofthe spinal-column segments is assured in every instance and that, if necessary, a relieving of stress on the frontal edges of the spinal column is achieved. The individual adaptation of the lengths of the individual frame parts of the orthotic device takes place in that rod elements 13, 14, which are located in receiving block 20, pushed into receiving block 20 in accordance with the individual requirements, are pulled out of it so that on the whole height and width can be individually adapted. To this end setscrews 17 already discussed earlier are first loosened. Then, rod a elements 13 and 14 can be moved relative to receiving block 20. As soon as the correct adjustment has been reached it is fixed by tightening setscrews 17.

Such an arrangement can be multiply provided in the frame orthotic device so that as a whole height, width, depth and angles allow themselves to be individually adapted.

The maximal possibility of movement of rod elements 13, 14 is limited by the given extension of oblong holes 15. This also assures that rod elements 13, 14 can not be drawn out of receiving block 20 in an unintentional manner.

It is advantageous if all parts of the thread connections are provided with a uniform screw system, that is, with the same threads, so that they can also be exchanged with each other if necessary.

The rod elements can be continuously adjusted both horizontally and vertically.

The reclination truss pads can be adjusted in height and in their angle up to 20 degrees.

The tilting of the chest and pelvic bars takes place via a more or less finely graduated adjustment selected to correspond to the particular requirements.

In order on the one hand to reduce the weight of the orthotic device and on the other hand to stabilize the flexing elasticity the rod elements can comprise recesses in their longitudinal direction and optionally even in deviation therefrom.

A sufficient tilting movement of the symphyseal truss pad can be achieved by an elastic plastic web.

The side paddings can be replaceable. This is advantageously achieved with VELCRO, hook and loop fasteners.

In order to achieve a reproducible adjustment both in the longitudinal direction and also in the case of angle adjustments, appropriate spacings can be provided for the longitudinal motion and the angles.

I claim:

1. Frame-construction hyperextension orthotic device to be worn by a human being comprising;

a substantially horizontal upper frame, said substantially horizontal upper frame having spaced apart first and second pads adapted and constructed to lie in abutment against each of the clavicles of said human being;

a substantially horizontal lower frame, said substantially horizontal lower frame having a third pad adapted and constructed to lie in abutment against the stomach of said human being;

a first vertical frame;

a second vertical frame;

said first vertical frame and second vertical frame being parallel and spaced from each other, said first vertical frame and said second vertical frame being connected by an adjustable belt, said adjustable belt having a fourth pad adapted and constructed to lie against the lower back of said human being;

each of said upper frame, said lower frame, said first vertical frame and said second vertical being constructed of elongated parts, said parts being linearly adjustable and being selectively retained in position by a fitment;

one end of said upper frame being connected to one end of said first vertical frame;

the other end of said upper frame being connected to one end of said second vertical frame;

the other end of said first vertical frame being connected to one end of said lower frame;

the other end of said second vertical frame being connected to the other end of said lower frame.

2. The frame construction of claim 1 wherein in each of the separable parts of the upper frame, the separable parts of the lower frame, the separable parts of each for the first vertical frame and second vertical frame have ends that are slidably mounted in said fitment comprising of tubular means, and each said tubular means is fitted with a set screw to limit movement of said ends in said tubular means when said set screws are tightened.

* * * * *